(12) United States Patent
Moore

(10) Patent No.: US 7,594,891 B2
(45) Date of Patent: Sep. 29, 2009

(54) PORTABLE PHYSIOLOGICAL PARAMETER MONITOR

(76) Inventor: Roy D. Moore, 1500 Marboro Dr., Greensboro, NC (US) 27406

( * ) Notice: Subject to any disclaimer, the term of this patent is extended or adjusted under 35 U.S.C. 154(b) by 0 days.

(21) Appl. No.: 11/321,987

(22) Filed: Dec. 29, 2005

(65) Prior Publication Data

US 2007/0156052 A1    Jul. 5, 2007

(51) Int. Cl.
*A61B 5/02* (2006.01)
*A61B 5/103* (2006.01)
*A61B 5/117* (2006.01)

(52) U.S. Cl. .............. 600/485; 600/500; 600/483; 600/481; 600/595

(58) Field of Classification Search .......... 600/300, 600/301, 490–504, 481, 483, 485, 595, 486; 482/8, 9, 142–147
See application file for complete search history.

(56) References Cited

U.S. PATENT DOCUMENTS

| | | | | |
|---|---|---|---|---|
| 3,664,666 A * | 5/1972 | Lloyd | .......................... | 482/133 |
| 4,112,928 A | 9/1978 | Putsch | | |
| 4,244,021 A | 1/1981 | Chiles, III | | |
| 4,278,095 A | 7/1981 | Lapeyre | | |
| 4,320,767 A * | 3/1982 | Villa-Real | ................. | 600/493 |
| 4,408,613 A | 10/1983 | Relyea | | |
| 4,715,296 A * | 12/1987 | Wilkinson | ............... | 108/116 |
| 4,856,775 A * | 8/1989 | Colledge et al. | ............ | 482/148 |
| 4,927,138 A * | 5/1990 | Ferrari | ........................ | 482/91 |
| 5,458,548 A * | 10/1995 | Crossing et al. | ............... | 482/6 |
| 5,524,637 A * | 6/1996 | Erickson | ...................... | 600/592 |
| 5,584,298 A * | 12/1996 | Kabal | .......................... | 600/485 |
| 5,743,268 A * | 4/1998 | Kabal | .......................... | 600/526 |
| 5,813,947 A * | 9/1998 | Densmore | .................... | 482/51 |
| 5,997,442 A * | 12/1999 | Cordes | ......................... | 482/52 |
| 6,361,501 B1 * | 3/2002 | Amano et al. | ............... | 600/500 |
| 7,008,350 B1 * | 3/2006 | Yamazaki et al. | ............. | 482/8 |
| 7,101,324 B2 * | 9/2006 | Matos | ......................... | 482/124 |
| 7,367,950 B1 * | 5/2008 | Masakov et al. | ............ | 600/483 |
| 2005/0037905 A1 * | 2/2005 | Matos | ......................... | 482/123 |
| 2006/0009698 A1 * | 1/2006 | Banet et al. | .................. | 600/485 |
| 2006/0063982 A1 * | 3/2006 | Sullivan et al. | ............. | 600/301 |
| 2007/0073558 A1 * | 3/2007 | Hall et al. | ....................... | 705/2 |
| 2007/0106127 A1 * | 5/2007 | Alman | ......................... | 600/300 |
| 2007/0142715 A1 * | 6/2007 | Banet et al. | ................. | 600/301 |
| 2007/0149883 A1 * | 6/2007 | Yesha | ......................... | 600/485 |

OTHER PUBLICATIONS

PCT Notification of Transmittal of the International Search Report and the Written Opinion of the International Searching Authority or the Declaration, Nov. 5, 2007, pp. 1-9.

* cited by examiner

*Primary Examiner*—Charles A Marmor, II
*Assistant Examiner*—Navin Natnithithadha
(74) *Attorney, Agent, or Firm*—Womble Carlyle Sandridge & Rice, PLLC; C. Robert Rhodes

(57) ABSTRACT

A microprocessor unit receives input data from a work measuring station, a sphygmomanometer, and a heart rate sensor and combines such data to provide output signals to a display device indicative of various physiological parameters relating to cardiovascular fitness such as heart work index, total peripheral resistance to blood flow, and caloric need. A carrying case for the aforesaid equipment converts into an exercise stool by means of folding or removable legs.

2 Claims, 7 Drawing Sheets

PORTABLE PHYSIOLOGICAL PARAMETER MONITOR

BACKGROUND OF THE PRESENT INVENTION

This invention relates to a portable health self-monitoring apparatus, and more particularly to an instrument for converting data input concerning work expended, pulse rate, and blood pressure into data indicative of various physiological parameters such as heart work index, total peripheral resistance to blood flow, and caloric need. In addition, the invention relates to a carrying case for the aforesaid instrumentation which converts into an exercise stool.

In recent years, more emphasis has been placed on health care, and particularly on home health care.

Additionally, particular attention is now being given to cardiovascular fitness. Various types of instrumentation are now available in the domestic market for measuring blood pressure, pulse rate, and heart rate.

This is pertinent raw data, but unless it is combined with other data and taken at precise times in conjunction with a controlled exercise program on a periodic basis it is not particularly helpful. A discussion of various physiological parameters may be helpful in understanding the problem.

First of all, one should be aware of the term "heart work index" which, as used herein, is a measure of the heart's ability to develop an economy of effort to accomplish a prescribed workload. Also, the heart work index estimates a tone in the myocardium (middle muscular layer of the heart wall) that produces more cardiac output. Over a period of time a decrease in the heart work index shows an improvement in the ability or efficiency of the heart muscle to perform a foot pound of body work. Heart rate recovery is the key to determining the heart work index in that it depicts the quickness with which the heart muscles restore the heart to its pre-stress status and also expresses the ability to quickly eliminate the toxic elements and waste that accumulated during the stress period.

The heart work index formula as utilized in the present invention is:

$$HWI = \left[ HR_1/WT + \frac{HR_2 + HR_3}{\text{Ft Lbs.}} \right] 100$$

Where:
HWI=heart work index
WT=weight of the subject
$HR_1$=resting heart rate
$HR_2$=heart rate immediately after exercise
$HR_3$=heart rate 1 min. 30 sec. after exercise
S (measured in ft. pounds)=the number of steps onto a one foot bench×the body weight×5 (complete step up and down of both feet onto and from bench=1 count
J (measured in ft. pounds)=distance in feet×body weight× 0.8 (walking or jogging)
H (measured in ft. pounds)=the number of steps (the number of times the left foot lands)×3×body weight×0.8 (walking or running in place)

Heart rate immediately after exercise ($HR_2$) should be taken within the first ten or fifteen seconds after the exercise routine is completed. Thus, the heart rate should be established during a relatively short span of sensing, because the heart rate tends to decrease at a faster rate after about twenty seconds into post stress period.

Total peripheral resistance which, as used herein, is the resistance to blood flow can be closely estimated by gauging the recovery ability of the heart rate during the post stress period. The change in the heart rate from a time immediately after exercise and a time one minute and thirty seconds after stress period also is indicative of the tone of the myocardium. Rapid recovery of the left ventricle is proportional to the economy of effort of the heart. Also, rapid recovery is proportional to ejectable force of the left ventricle which is inversely related to total peripheral resistance.

The formula for total peripheral resistance is:
TPR=mean blood pressure divided by heart rate recovery expressed as a percentage.

The formula used to calculate mean blood pressure in medical schools and nursing schools is systolic blood pressure minus diastolic blood pressure divided by three then added to the diastolic blood pressure. The heart rate recovery expressed as a percentage is the difference between the heart rate immediately after a three minute exercise and the heart rate after one minute and thirty seconds following the exercise period divided by the resting heart rate and all multiplied by one hundred.

Thus the entire formula for total peripheral resistance is written as:

$$TPR = \left[ \frac{SBP - DBP}{3} + DBP \right] \div HR_4 \times 100.$$

where:
SBP=systolic blood pressure
DBP=diastolic blood pressure
$HR_1$=resting heart rate
$HR_2$=heart rate immediately after three minutes exercise
$HR_3$=heart rate one minute and thirty seconds after completion of the three minute exercise $$HR_4 = \frac{HR_2 - HR_3}{HR_1} \times 100$$

Caloric usage is another parameter which is very helpful to persons on an exercise or exercise/diet program. Diet programs are interrelated with caloric intake and usage. Therefore it is advantageous to be able to determine caloric usage during a particular exercise regime. The pertinent formula for determining caloric usage is to divide the work in foot pounds done by 3,172 to obtain the calories used. Thus, if a person is stepping up onto a one foot high stool repeatedly, the formula for determining the calories used is to multiply the number of steps by the weight of the person, all of which is divided by 3,172. Likewise, if the person is jogging, the distance in feet is multiplied by the weight of the individual times 0.8 (coefficient of friction), all of which is divided by 3,172. Thirdly, if the person is jogging in place, the formula for determining caloric usage is. caloric usage equals number of left steps times 3 times weight times 0.8 divided by 3,172.

BRIEF SUMMARY OF THE INVENTION

Presently, applicant is not aware of any instrumentation which combines a sphygmomanometer and heart rate sensor with an exercise device, from which information is fed to a microcomputer to determine such cardiovascular fitness related physiological parameters as total peripheral resistance, heart work index, or caloric usage. Instrumentation which is known includes the disclosures in U.S. Pat. No. 4,244,021 to Chiles; U.S. Pat. No. 4,278,095 to Lapeyre; U.S. Pat. No. 4,408,613 to Relyea; and U.S. Pat. No. 4,112,928 to Putsch. These references do not include a sphygmomanometer, nor do they convert the raw data to cardiovascular fitness related parameters.

The present invention provides such instrumentation. In addition to a monitoring means for sensing body functions such as blood pressure and heart rate and generating electrical data pulses responsive thereto, the present invention includes a pressure sensitive switching means for counting repetitions of a prescribed exercise and generating another set of electrical data pulses responsive thereto. All such data pulses are delivered as inputs to a microprocessor means, which also includes a clock means, which combines the aforesaid electrical data pulses to provide output signals representative of such physiological parameters such as heart work index, total peripheral resistance, and/or caloric usage. The output signals are provided to a display means which converts them to visually perceptible readouts thereon.

A specially designed carrying case, which generally resembles a briefcase, not only carries all of the aforesaid instrumentation, but also converts into an exercise stool approximately one foot high. The stool includes an enclosure having front and rear walls, end walls, a bottom wall, and a top wall hinged along one edge to the upper edge of the rear wall. A set of movable or removable legs converts the enclosure or case from a carrying case to the exercise stool of a prescribed height.

It is therefore an object of the present invention to provide a portable, self-health monitor for measuring, computing, and displaying various cardiovascular fitness parameters.

It is another object of the present invention to provide a health monitor of the type described which may be utilized in conjunction with a specially designed apparatus to effect a prescribed, measurable exercise program.

Another object of the present invention is to provide a monitor of the type described which includes a work measurement device and a body function monitor, the outputs of which are sensed by a microprocessor and visually displayed.

Other objects and a fuller understanding of the invention will become apparent from reading the following detailed description of a preferred embodiment along with the accompanying drawings in which:

DETAILED DESCRIPTION OF A PREFERRED EMBODIMENT

Figure 1:
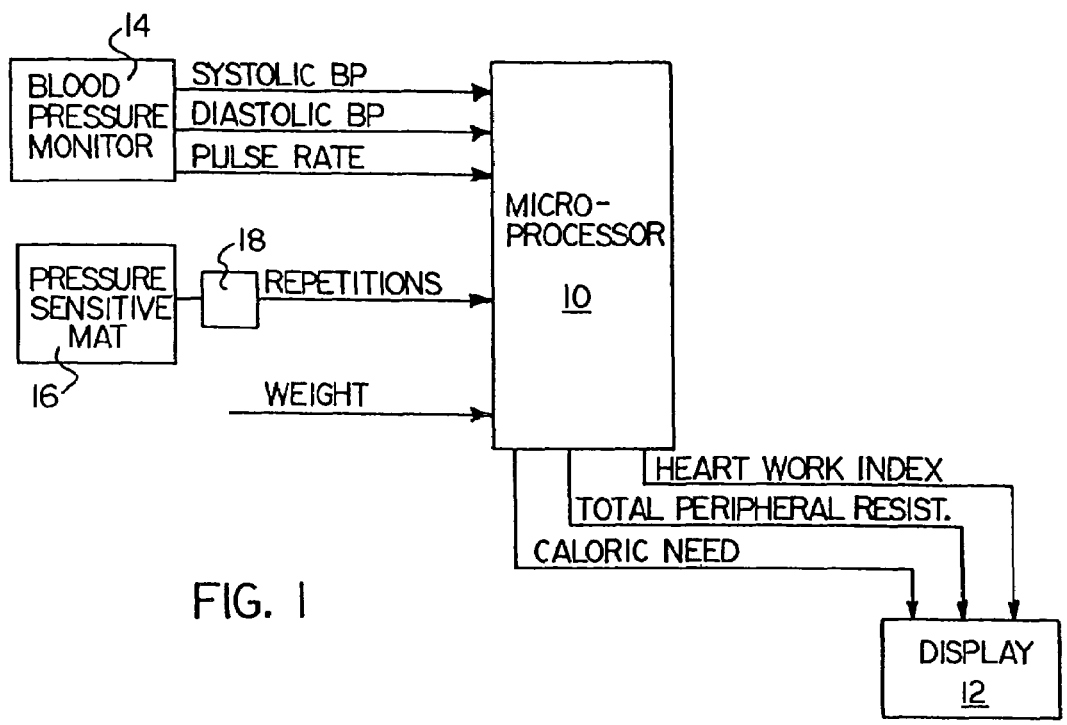
FIG. 1 is a schematic representation of the monitoring system according to the present invention.

Turning now to FIG. 1, there is illustrated schematically the portable health monitor according to the present invention. A central processing unit 10 is provided which, in general, receives input signals of various types (blood pressure, pulse rate, and work expended) performs certain prescribed calculations thereon and delivers signals representative of the results to a display device 12. The cardiovascular fitness parameters then shown on display 12 are indicative of such body functions as heart work index, total peripheral resistance, and caloric usage during prescribed exercises.

A monitor 14 is suitably and operably attached to the subject to be monitored and includes means associated therewith for sensing such body functions as a blood pressure and heart rate, and generating a set of electrical data pulses responsive thereto. Such sphygmomanometer and heart rate counters are presently commercially available on the open market in portable sizes. The sphygmomanometer portion of such apparatuses provide both systolic blood pressure and diastolic blood pressure. For purposes of this invention, the sphygmomanometer and heart rate counter should be incorporated in the same instrument, if possible.

A pressure sensitive switching means 16 counts the repetitions of a prescribed exercise and generates a first set of electrical data pulses responsive thereto.

For example, the pressure sensitive means may be a mat having a switch therein which counts steps during jogging in place or repeated stepping up onto and down from a stool of prescribed height. To detect the steps, a special mat is used which has a normally opened set of contacts incorporated therein. When pressure is applied to the mat 16, or a prescribed area of the mat, the contacts close. Conversely when the pressure is released the contacts open. If the closing of the contacts are fed directly to the central processing unit, the operation may malfunction, probably due to one or more static charges or built-up capacitance that causes the high impedance device of the computer to operate improperly. Thus, an interface 18 of known configuration is constructed which includes a relay operated directly from the contacts. The energization of the relay properly imparts one signal to the computer, then ensures that another signal is not imparted until the next step or closure of the contacts.

The central processing unit 10 (FIG. 2) may be any one of a number of types of microcomputing units. The system shown in FIG. 2 is the basic Microcomputer Module—Evaluation Kit 2 manufactured and marketed by Motorola, Incorporated. The central processing unit (CPU) 10 is programmed to receive data from the blood pressure and pulse rate monitor 14, the pressure sensitive mat 16, and manual input concerning weight of the subject. The CPU 10 then calculates the input data according to a prescribed program, and provides output data signals to the display unit 12 indicative of heart work index, total peripheral resistance, and caloric usage. The data is input at connector J1, and output through connector J2 (FIG. 2).

Within the central processing unit, information as to the heart rate at rest, immediately after exercise, and one minute and thirty seconds after exercise are received and combined with other information concerning weight and number of steps and type of exercise to determine the heart work index according to the formula:

$$HWI = \left[ HR_1 / WT = \frac{HR_2 + HR_3}{\text{Ft. Lbs.}} \right] 100$$

HWI=heart work index
WT.=weight of subject
$HR_1$=resting heart rate
$HR_2$=heart rate immediately after exercise
$HR_3$=heart rate one minute and thirty seconds after exercise In addition, a switch 30 on the display unit 10 is set to one of three positions depending upon whether the subject is stepping up and down on a bench (indicated by a position "S"); whether the subject is jogging or walking (indicated by position "J"); or whether the subject is running in place (indicated by position "H").

Within the program, where the switch 30 is placed in position "S," the number of bench steps are multiplied by body weight times 5 (a complete step up and down of both feet equaling one count). Similarly, whether the subject is walking or jogging, the input to the central processing unit is distance in feet walked times the body weight times 0.8. Finally, in position H, the work or foot pounds entry into the computer is developed as being the number of steps (number each time the left foot lands) times 3 times the weight times 0.8 (the factor 0.8 is considered to be the average coefficient of friction utilized when jogging).

The second body function, i.e. total peripheral resistance, which is the resistance to blood flow can be closely estimated by gauging the recoverability of the heart rate during the post stress period. Thus, the difference between the resting heart rate, the heart rate immediately after exercise, and the heart rate one minute and thirty seconds after exercise indicate the tone of the myocardium. The recovery rate of the left ventrical is proportional to the economy of work effort of the heart. Rapid recovery is also proportional to the ejectable force (blood pressure) of the left ventrical which is inversely related to total peripheral resistance. Thus the total peripheral resistance is measured in accordance with the following formula:

$$TPR = \left[ \frac{SBP - DBP}{3} + DBP \right] \div HR_4 \times 100$$

where:
SBP=systolic blood pressure
DBP=diastolic blood pressure
$HR_1$=resting heart rate
$HR_2$=heart rate immediately after three minutes exercise
$HR_3$=heart rate one minute and thirty seconds after completion of the three minute exercise $$HR_4 = \frac{HR_2 - HR_3}{HR_1} \times 100$$

Where the above formula is a result of less than 0.85 there is an indication of a healthy heart. On the other hand, where the result of the formula above is greater than 1.65, there is an indication that the resistance to blood flow is too high.

The last body function which is measured by the apparatus of the present invention is caloric usage or the number of calories expended during a prescribed exercise program. The ability to determine caloric usage is very important as far as maintaining a planned diet is concerned, because a diet program should take into consideration the weight of the person and the activity level of one's lifestyle. A diet schedule alone is not sufficient to assure one of maintaining optimal body muscle and organ tone. Losing weight should be a gradual process as the abrupt loss of weight may result in the distorted metabolic processes, and weakened tissues and vital organs. While exercise is a necessary adjunct to a planned diet program, it is advantageous to be able to measure the amount of work done in term of calories expended during any particular exercise routine.

The present apparatus measures very accurately the diately caloric usage of any prescribed exercise by combining the amount of exercise with the weight of the person multiplied by a factor determined by the type of exercise being conducted. For example, in a bench stepping exercise, the number of complete steps is sensed by the mat 16 and multiplied by the weight to determine the amount of work done. This figure is then divided by 3,172, which is the factor for converting foot pounds into calories expended. Likewise, in a jogging exercise the distance in feet is multiplied by the weight of the individual and by a factor of 0.8 (coefficient of friction), again all divided by the conversion figure 3,172. In an exercise for jogging in place, the number of times the left foot engages sensing mat 14 is multiplied by 3 (each left step equals three feet) times the weight of the individual times 0.8, all divided by 3,172.

Figure 5:
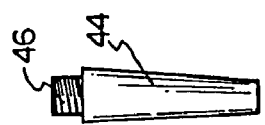
FIG. 5 is a perspective view illustrating one of the legs removed from the lower wall of the carrying case of FIG. 4.
Figure 3:
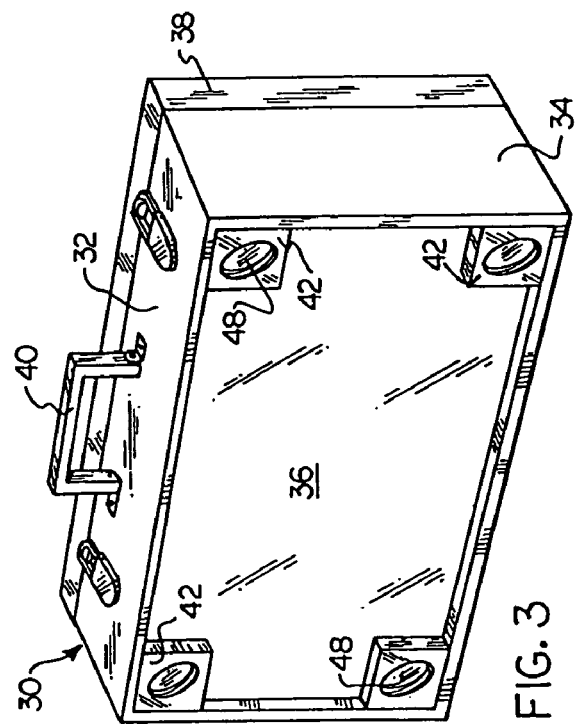
FIG. 3 is a perspective view looking at the front, one end, and underside of a first embodiment of a carrying case adapted for the present invention.
Figure 4:
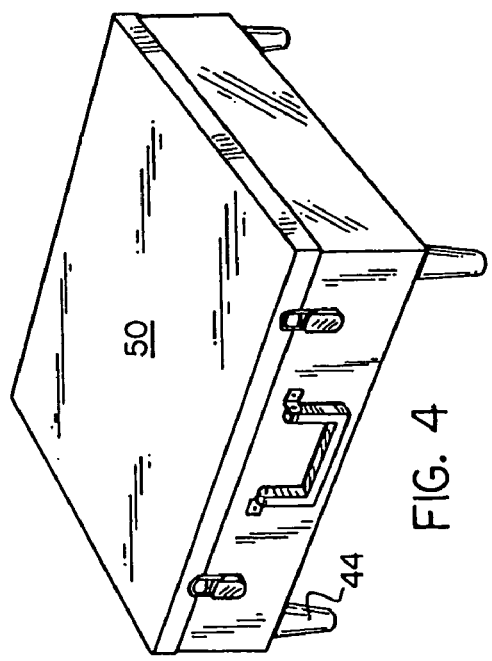
FIG. 4 is a perspective view similar to FIG. 3, except showing the front, one end, and top of the carrying case in the assembled position.

Turning now to FIGS. 3-5 there is illustrated a carrying case 30 which converts into an exercise stool of a prescribed height (preferably one foot). Toward this end, the carrying case 30 includes a pair of opposed side walls 32, a pair of opposed end walls 34, a lower wall 36, and a cover 38 hinged to one of the side walls 32. A handle 40 is provided on the side wall 32 opposite the side wall to which the cover 38 is hingedly attached. Lower wall 36 includes a mounting block 42 at each corner thereof for releasably mounting the removable supporting legs 44. Toward this end, legs 44 include an upstanding, threaded protuberance 46 which screws into a threaded passageway 48 in each mounting block 42. Thus; the legs. 44, when assembled form the bench illustrated in FIG. 4. The dimensions of the case 30 and legs 44 are such that, when assembled, the bench presents a stool surface 50 exactly one foot in height. The pressure sensitive mat 14 is then placed upon the surface 50 for the exercise program.

Figure 6:
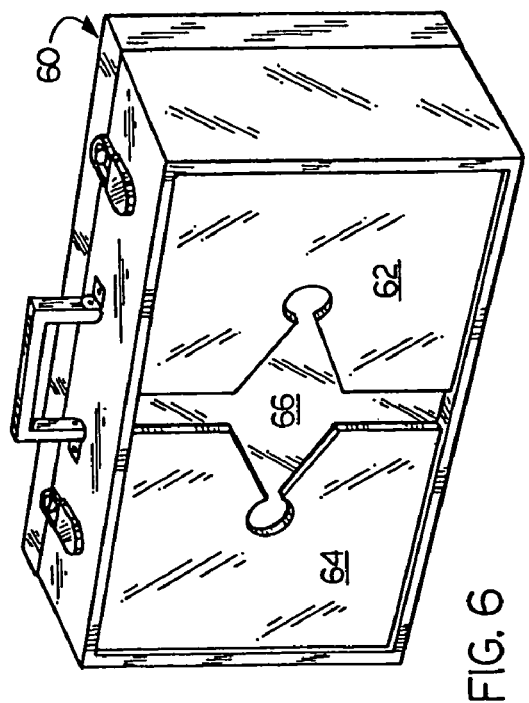
FIG. 6 is a perspective view, looking at the front, one side, and bottom of a second embodiment of the carrying case for the present invention.
Figure 7:
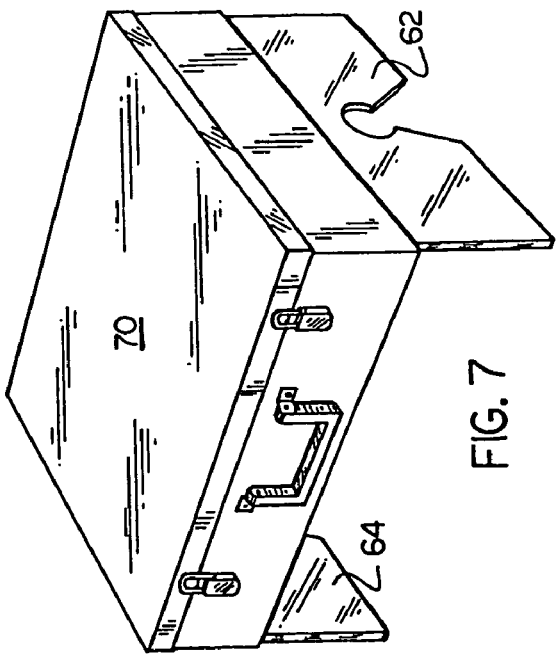
FIG. 7 is a perspective view, similar to FIG. 6, except showing the front, one side, and top of the carrying case in the assembled position.

In FIGS. 6 and 7, there is illustrated an alternative embodiment of the carrying case 60 which is similar to carrying case 30, except that a pair of leg members 62,64 are hingedly attached to lower wall 66 and fold outwardly therefrom to form the legs of the stool 60. Again, the legs 62,64 and the dimensions of the carrying case are such that the surface 70 of stool 60 is positioned one foot above the ground or floor level when the legs 62,64 are folded into the open position as illustrated in FIG. 7.

The carrying cases 30 (FIGS. 3-5) and 60 (FIGS. 6 and 7) carry the central processing unit 10, the display unit 12, the blood pressure and pulse rate monitor 14 and the pressure sensitive mat 16 therein when not in use. Also, the case 30 carries the removable legs 44 of the embodiment illustrated in FIGS. 3-5 when not in use.

Figure 8:
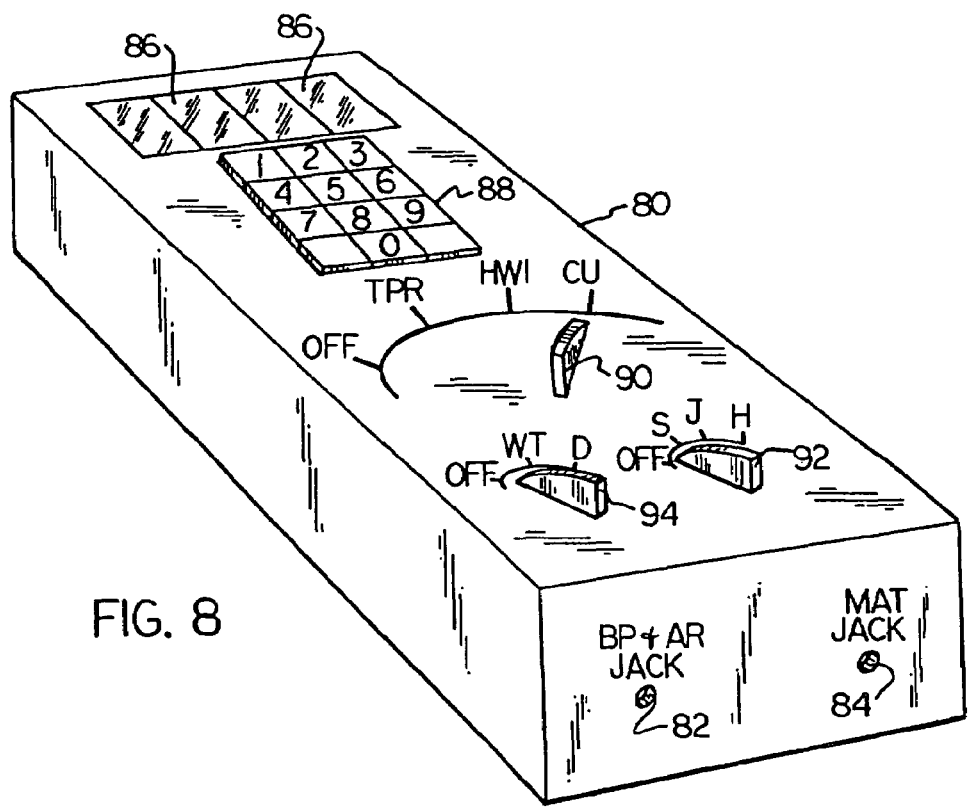
FIG. 8 is a perspective view illustrating the housing which contains the central processing unit.
Figure 2A:
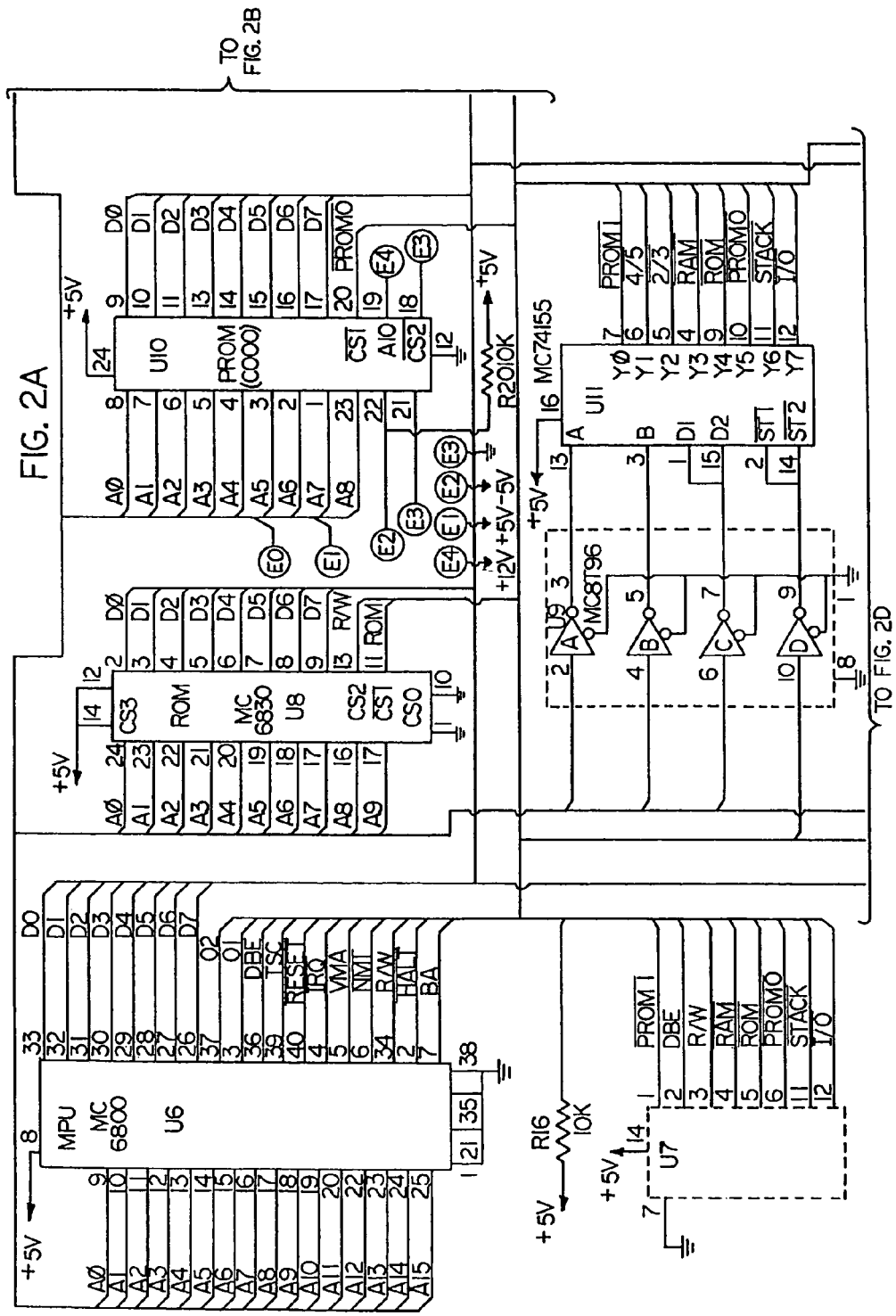
FIGS. 2A-2E collectively is an electrical schematic of the microprocessor unit and visual display units.
Figure 2B:
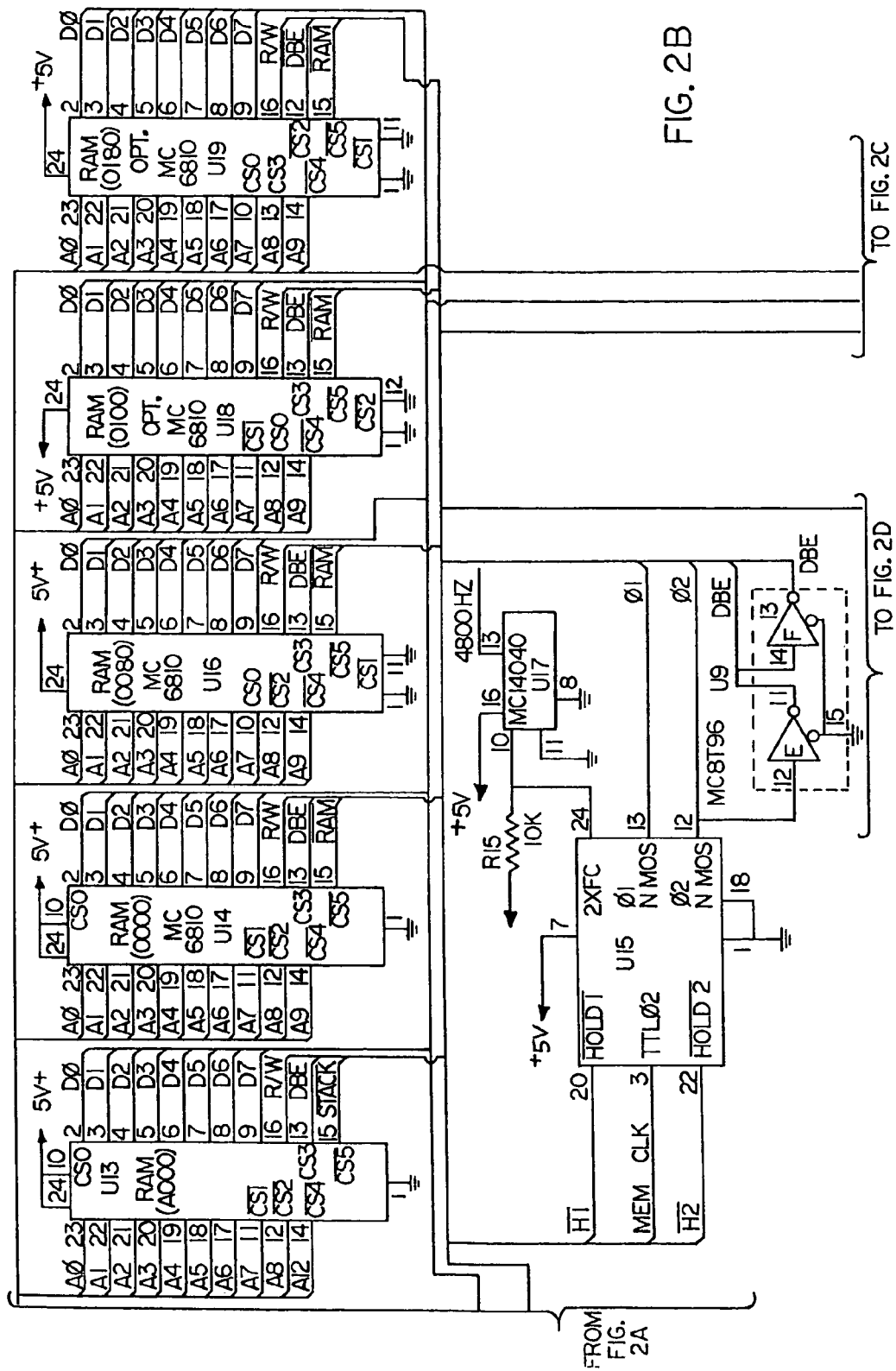
Figure 2C:
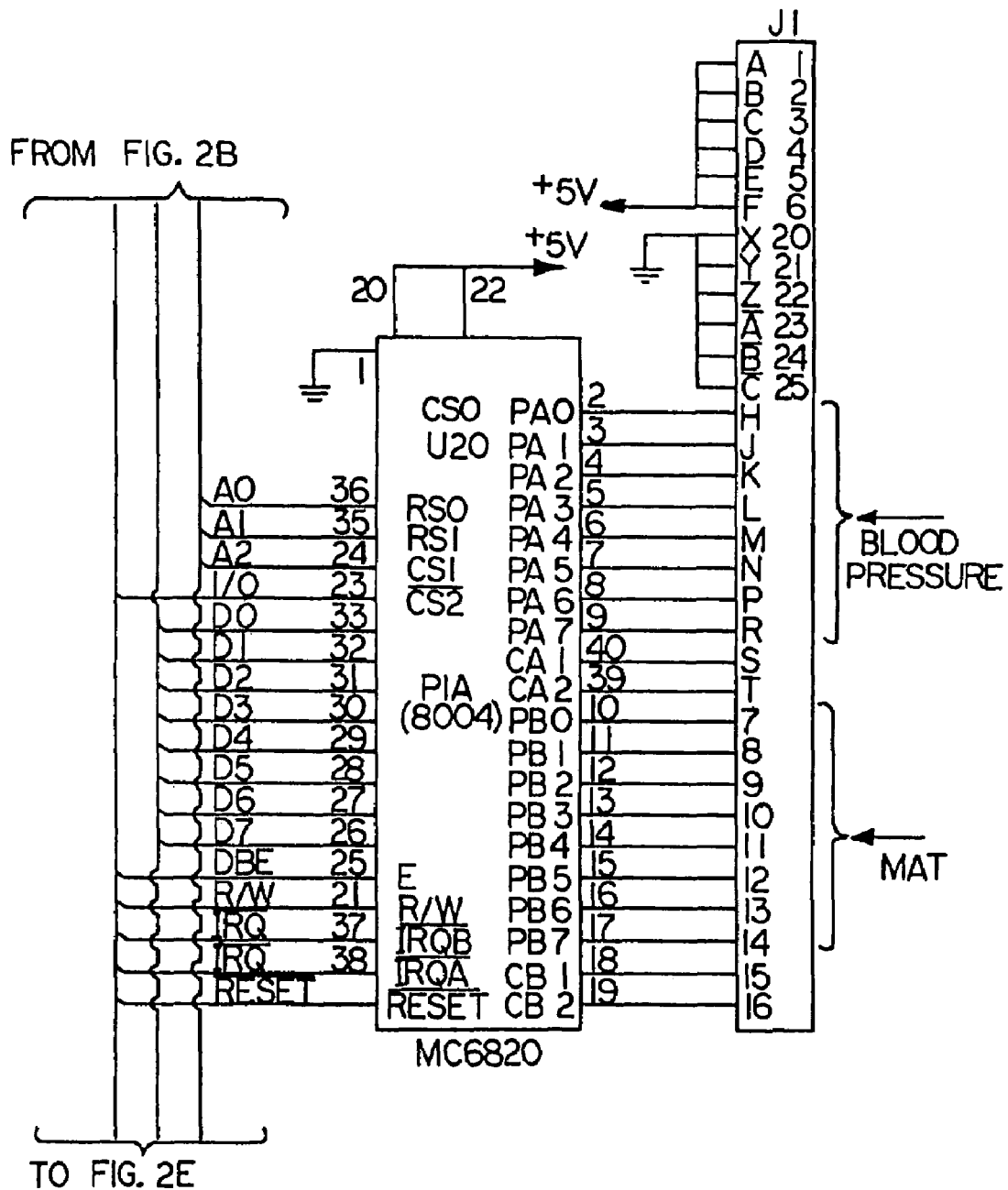
Figure 2D:
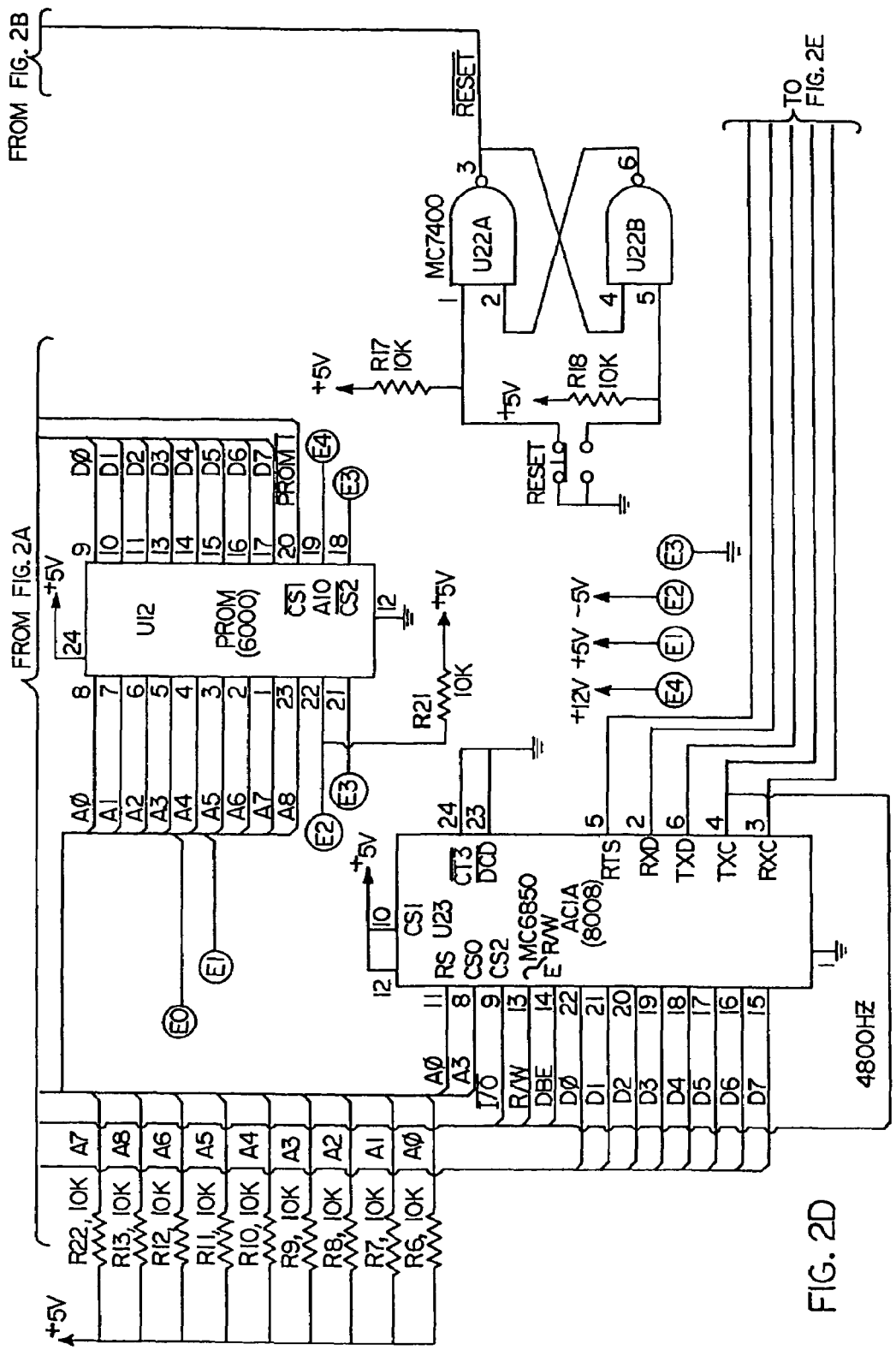
Figure 2E:
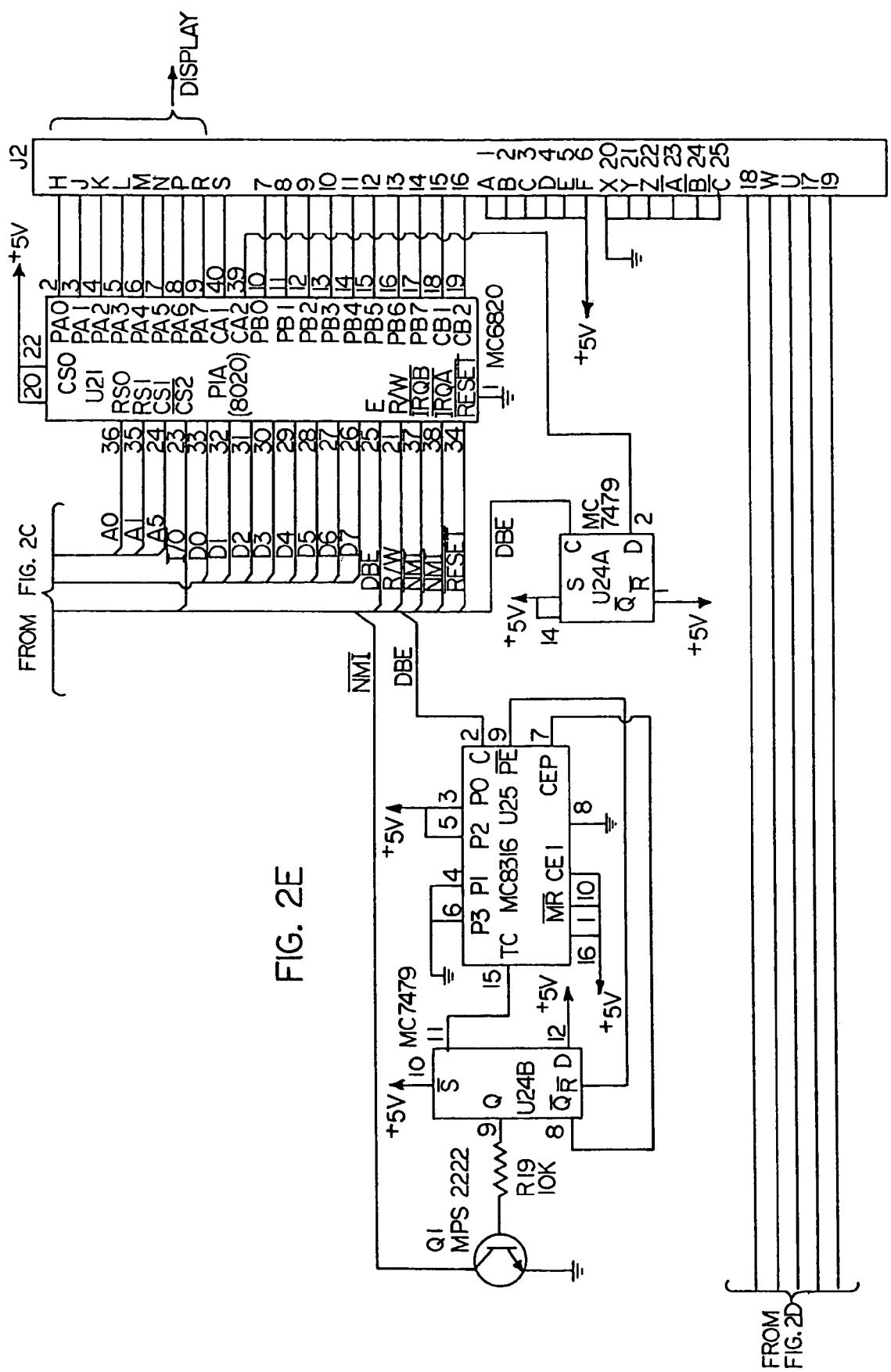

Turning now to FIG. 8, there is illustrated the housing 80 which contains the central processing unit 10 and visual display unit 12 therein. While these two units might be contained in separate housings, there is no particular need for such separation, and preferably the two units are combined into the housing 80. A first jack 82 receives the connecting wire extending from the blood pressure and heart rate monitor 14.

The second jack 84 receives the connecting wire from the pressure sensitive mat 16, which extends through control relay 18.

A plurality of numerical displays 86 are provided on the face of housing, 84 providing a visual display to the person utilizing the device or anyone else monitoring for him or her. Either LCD or LED display units may be provided, and it is felt that four such units will suffice for normal usage, although more may be provided if necessary. A set of digital input switches 88 are provided for providing such input as weight and distance. Three selector switches 90,92, and 94 are provided. Switch 90 allows the operator to indicate to the unit whether total peripheral resistance, heart work index, or calories used is the desired output. By returning the switch to "OFF," all previous inputs are cleared. Switch 94 allows the operator to indicate to the central processing unit the type of exercise being performed whether it is stepping, jogging, or jogging in place. Again, by returning the switch to the "OFF" position, all previous inputs are erased. Switch 94 is utilized in conjunction with the digital input switch 88 to provide input to the central processing unit indicative of the weight of the person being monitored and/or the distance that the person has walked or jogged. Again, by returning to the switch to "OFF," all previous inputs are cleared.

There is thus described in detail a preferred embodiment of the portable health self-monitor contemplated by the present invention. It is obvious that while a preferred embodiment has been described in detail hereinabove, certain modifications and changes might be made, without departing from the scope of the invention, which are set forth in the claims below.

What is claimed is:

1. A combination portable exercise device/health monitor for measuring, computing, and displaying various physical fitness characteristics occurring in conjunction with exercise comprising:
   a) a pressure sensitive switching mat which counts repetitions of exercise steps by a user onto the exercise device from a support surface and generates a first set of electrical data pulses responsive thereto;
   b) a body function monitor which senses both systolic and diastolic blood pressure and heart rate, and generates a second set of electrical data pulses responsive thereto;
   c) an input device having at least two switches for receiving manually input data that includes the weight of the user and the type of exercise steps;
   d) a central processor including clock, data storage, and computing unit for receiving the first set of electrical data pulses from the pressure sensitive switching mat over a period of time and the second set of electrical date pulses from the body function monitor at prescribed times in conjunction with the exercise steps, and for combining the first and second electrical data pulses with the manually input data from the input device according to preset formulas in the central processor to provide output signals representative of the user's physiological parameters comprising heart work index, total peripheral resistance, and calories expended;
   e) a display unit receiving the output signals and converting them to visually perceptible readouts thereon; and
   f) an exercise device in the form of a carrying case comprising a housing and cover forming an enclosed chamber of a suitable size to carry the pressure sensitive switching mat, body function monitor, central processor, input device, and display unit; the housing and cover when closed, forming an exercise stool having an upper surface selectively receiving and supporting the pressure sensitive switching mat during the exercise at a prescribed distance above the support surface.

2. The combination portable exercise device/health monitor according to claim 1 wherein said housing comprises:
   a) opposed front and rear walls, end walls, a bottom wall, a top wall hinged along one edge to the upper edge of said rear wall, and a carrying handle on said front wall forming a compartment for the pressure sensitive switching mat, the body function monitor, the central processor, and the display unit; and
   b) a set of collapsible or removable legs for converting the enclosure from a carrying case to an exercise stool.

* * * * *